United States Patent [19]

Chee et al.

[11] Patent Number: 5,380,307
[45] Date of Patent: Jan. 10, 1995

[54] CATHETER WITH ATRAUMATIC DRUG DELIVERY TIP

[75] Inventors: U. Hiram Chee, Palo Alto, Calif.; Edward R. LeMoure, New Haven, Conn.

[73] Assignee: Target Therapeutics, Inc., Fremont, Calif.

[21] Appl. No.: 954,669

[22] Filed: Sep. 30, 1992

[51] Int. Cl.⁶ .................... A61M 5/00; A61M 25/00
[52] U.S. Cl. .................... 604/264; 604/266; 604/43
[58] Field of Search ............... 128/656, 657, 658, 772; 604/43, 48, 40, 52, 53, 54, 169, 264, 246, 165, 167, 164, 170, 30, 33, 49, 249, 256, 266, 267, 280

[56] References Cited

U.S. PATENT DOCUMENTS

| | | |
|---|---|---|
| 3,593,713 | 7/1977 | Bogoff et al. |
| 4,149,535 | 4/1979 | Volder .................... 604/43 |
| 4,318,402 | 3/1982 | Vaillancourt . |
| 4,391,276 | 7/1983 | Lazarus et al. .................... 604/266 |
| 4,717,379 | 1/1988 | Ekholmer . |
| 4,739,768 | 4/1988 | Engelson . |
| 4,808,158 | 2/1989 | Kreuzer et al. .................... 604/49 |
| 4,842,590 | 6/1989 | Tanabe et al. .................... 604/282 |
| 4,848,344 | 7/1989 | Sos et al. .................... 606/94 |
| 5,158,084 | 10/1992 | Ghiatas .................... 128/657 |
| 5,259,847 | 11/1993 | Trambert .................... 604/164 |
| 5,273,523 | 12/1993 | Sozuki et al. .................... 604/43 |
| 5,279,542 | 1/1994 | Wilk .................... 604/19 |

FOREIGN PATENT DOCUMENTS 0299622  1/1989  European Pat. Off. ............ 604/280

*Primary Examiner*—John D. Yasko
*Assistant Examiner*—V. Alexander
*Attorney, Agent, or Firm*—Morrison & Foerster

[57] ABSTRACT

The catheter with atraumatic drug delivery tip can be sued to access remote tortuous blood vessels and to deliver defined doses of medication over a desired length of the accesses vessel. The guidewire of the catheter helps guiding the catheter to a desired location and can be used to control release of medication in axial as well as in radial direction inside the vessel. The catheter is designed with sections of different flexibility.

17 Claims, 3 Drawing Sheets

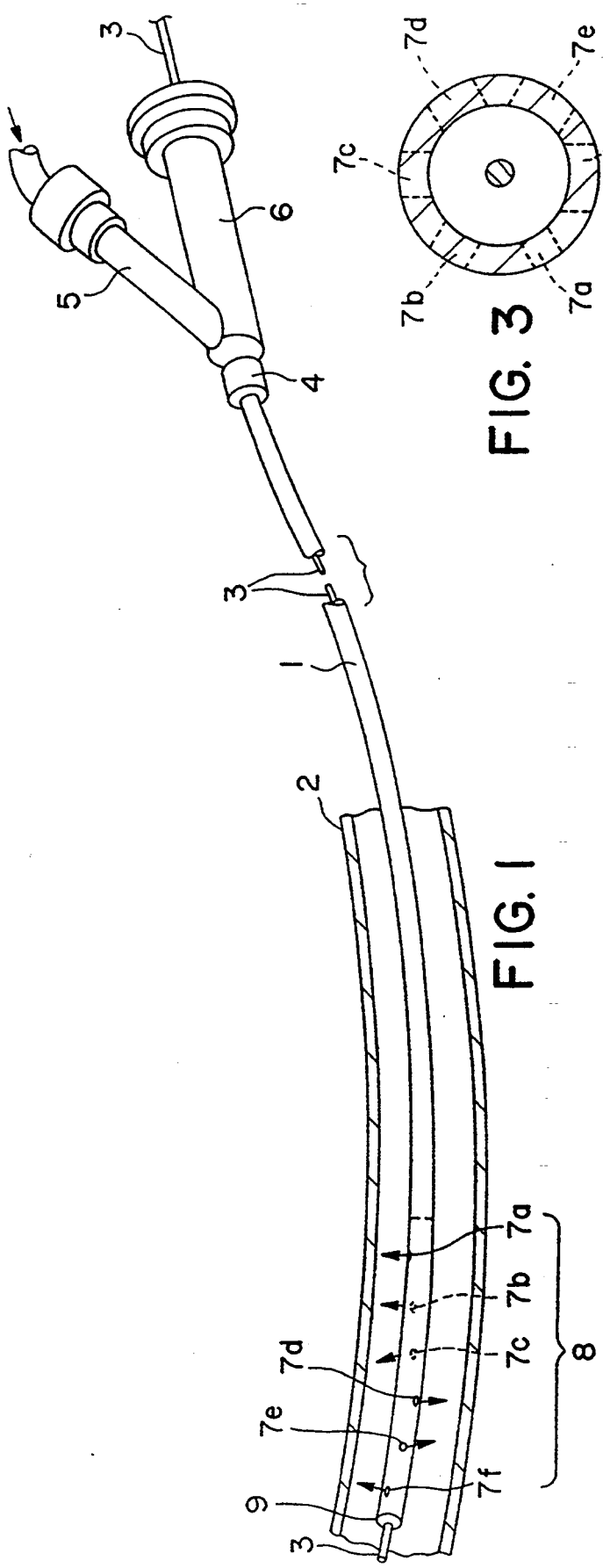
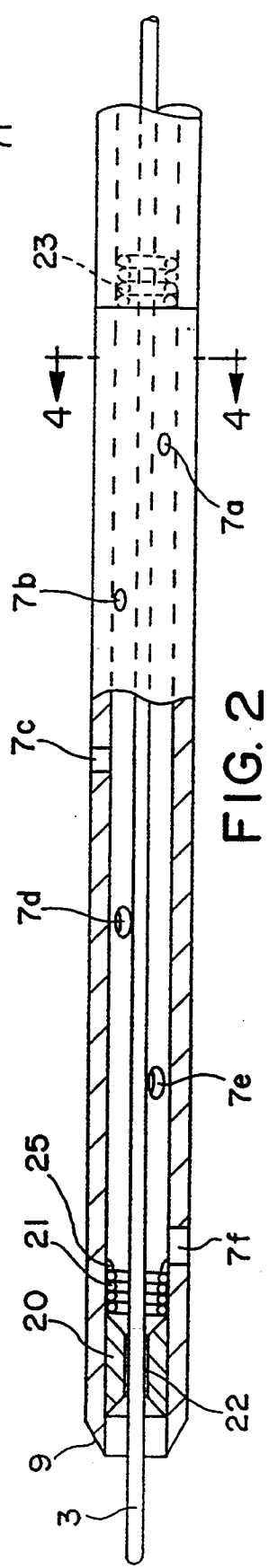

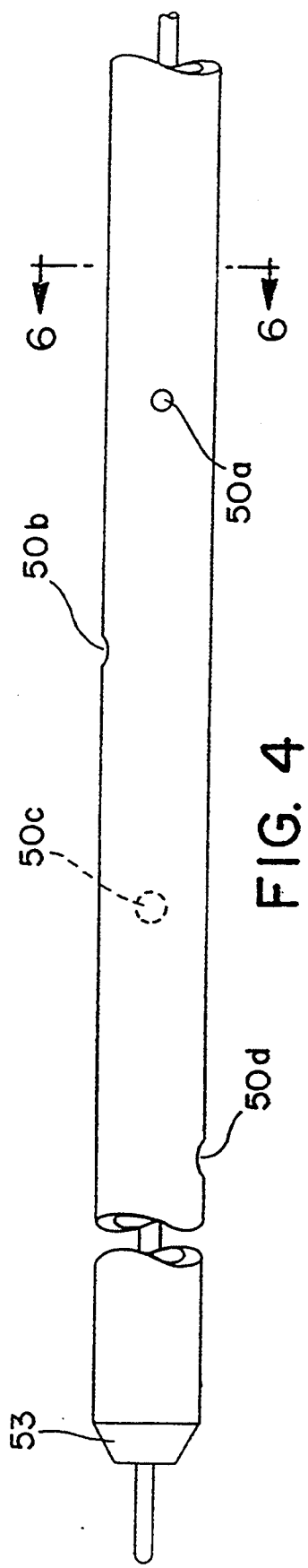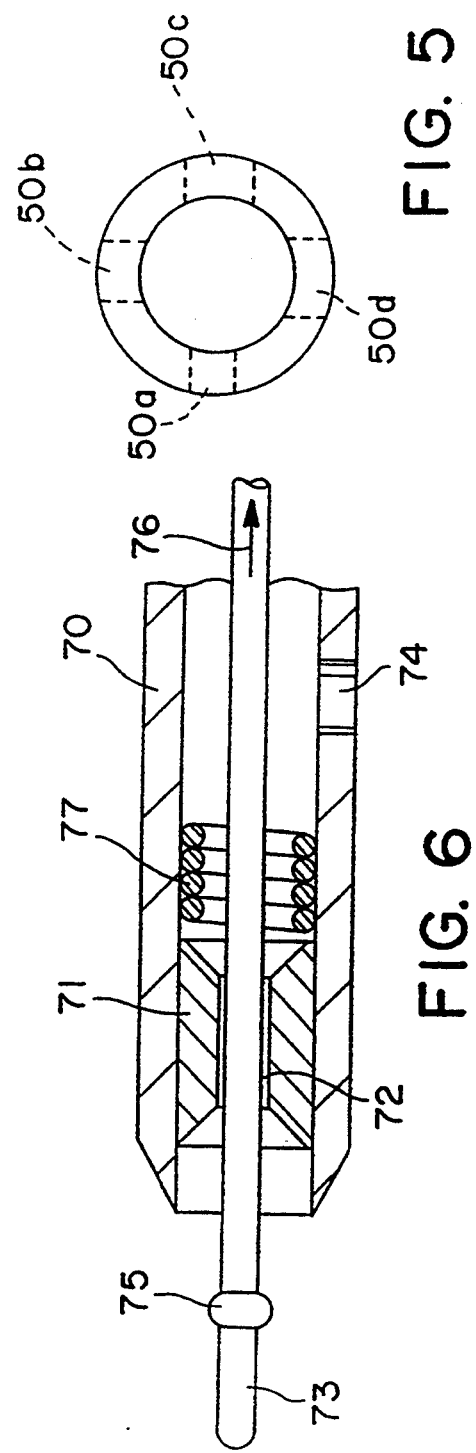

CATHETER WITH ATRAUMATIC DRUG DELIVERY TIP

BACKGROUND OF THE INVENTION

The catheter of the present invention is a new type of catheter for controlled dispensing of fluids in remote areas of a body.

Catheters for dispensing fluids in remote areas of a body are used in a variety of different clinical procedures. Some of these procedures require delivery of contrasting fluids for x-ray procedures, other procedures require delivery of medication at remote locations accessible through blood vessels.

Catheters are inserted either directly or with the help of guidewires. In either case the distal end section has to include means for guiding the device through blood vessels to the destination location without causing damage. Many different implementations for the distal end sections of guidewires and catheters are available. There are catheters available with sideholes for providing a temporary flow channel through a closed vessel. In such an application the sideholes upstream to the closure provide entrance of blood, the sideholes downstream of the closure provide for the exit of blood. In such an application the sideholes and the catheter have to be a size to allow sufficient flow-through for the closed vessel.

Another type of catheter with a plurality of sideholes has each of the sideholes connected to a separate lumen. Such a catheter allows to administer different medications at remote locations and at independent rates. Such catheters have a large outside diameter and are relatively stiff.

Large diameter catheters and catheters with large sideholes or with sideholes connected to separate lumens are too stiff and large for use in cerebral vessels or to remain overnight in a coronary artery of a beating heart artery. They do not include the multi-purpose applicability as needed for treatment of heart ailments including penetration of blood clots, dissolution of blood clots and dispensation of medication at desired rates over a desired length of a blood vessel.

The catheter of the present invention overcomes these and other disadvantages of the available catheters.

OBJECTS OF THE INVENTION

It is an object to this invention to provide for means for dispensing medication in remote areas of the vascular system and other body passageway systems.

It is another object of this invention to provide for means for dispensing medication in remote and very narrow passageways of a body.

It is still another object of this invention to provide for means for dispensing medication in remote areas of a body, whereby these means exhibit increasing flexibility from the proximal end to the distal end.

It is another object of this invention to provide a catheter including means for a preferred radial dispensation of medication.

It is another object of this invention to provide a catheter including means for axial and radial dispensation of medication.

It is still another object of this invention to provide a catheter for low pressure radial dispensation of medication.

It is still another object of this invention to provide a catheter for high pressure radial dispensation of medication.

It is still another object of this invention to provide a catheter with means for controllable axial dispensation of medication.

It is still another object of this invention to provide a catheter with means for controlling the location and length over which medication is radially dispensed inside a vessel.

It is still another object of this invention to provide for a catheter including means for even distribution of medication along a length of the distal end section of the catheter.

It is still another object of this invention to provide for a catheter with radiopaque markers and means for controllable radial and axial dispensation of medication.

DESCRIPTION OF THE INVENTION

The catheter of the present invention includes a long flexible, tubular body of graduated stiffness along the length of the body. A flexible distal end section ensures safe tracking of the catheter over a guidewire inserted into tortuous blood vessels. The increased stiffness along the length of the catheter from the distal end to the proximal end transmits axial force for easy advancement of the catheter in the vessel. A guidewire may be advanced to the desired location first and the catheter may be advanced in the vessel over the preinserted guidewire in a follow-on step. In another application the guidewire and catheter are advanced gradually in a sequential manner through tortuous blood vessels until the desired site is reached. A radiopaque marker in the distal end section of the guidewire and the catheter may help visualize advancement of the catheter to the desired location by fluoroscopy. The catheter of the present invention is characterized by an increasing stiffness along its length from the distal end section to the proximal end. The stiffness of the catheter may continuously change over the full length of the catheter or over one or more sections of the catheter. In the latter representation, an outer tubing extending over the whole length of the catheter due to the use of stiffer inner material occur swiftly over a finite length of the catheter and provides integrity to the construction of the catheter.

The distal end section of the catheter is provided with holes of different diameters arranged in a spiral over a finite length of the distal end section. These hole sizes are selected for a near equal radial ejection of medication from each hole over the distal end section of the catheter at specified flow rate ranges. The tip of the distal end section includes a center opening for the guidewire and for axial dispensation of medication. The tip of the distal end section is further formed for easy penetration of blood clots in the vessel. In one version of the catheter a reduction of diameter at the tip of the distal end section is combination with the guidewire form a seal to control the amount of axially released medication. In another version the guidewire includes an enlargement slightly smaller than the inner diameter of the distal end section of the catheter. Moving the enlargement of the guidewire inside the distal end section of the catheter controls the length over which medication is radially dispensed through the holes in the distal end section of the catheter.

For easy observation the enlargement of the guidewire may include the features of a radiopaque marker.

To dispense medication even in very small vessels this catheter may have an outer diameter of only 2F, or 0.66 millimeter. Catheters may have a length between 30 and 200 centimeters, with a preferred length at about 150 centimeters. The infusion section length may be from 0.5 centimeters to 30 centimeters.

In low pressure applications such as delivered by an infusion pump the catheter of the present invention can be used without a guidewire for optimum flow rate of medication, equally distributed over the infusion length. In high pressure applications, such as delivered by a syringe, the guidewire is most useful for controlling the axial ejection of medication.

DESCRIPTION OF THE DRAWINGS

FIG. 1 is an illustration of a perfusion catheter operationally placed in a blood vessel.

FIG. 2 is an illustration of the distal end section of the perfusion catheter.

FIG. 3 is a cross-sectional view of the distal end section of the perfusion catheter.

FIG. 4 is an illustration of the distal end section of another perfusion catheter.

FIG. 5 is a cross-sectional view of the distal end section of FIG. 4.

FIG. 6 is a detailed illustration of the distal end section of the perfusion catheter with a guidewire having an enlarged section for controlling the axial dispensing hole.

DESCRIPTION OF THE PREFERRED EMBODIMENT

Figure 7:
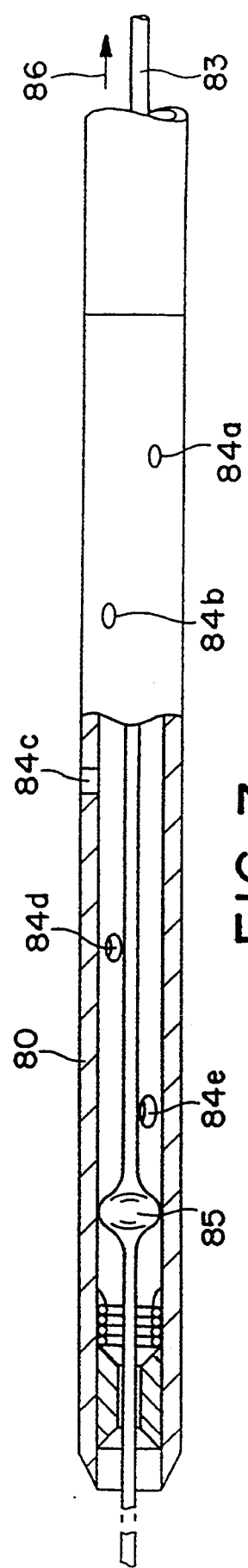
FIG. 7 is a detailed illustration of the distal end section of the perfusion catheter with a guidewire having an enlarged section for controlling the radial and axial dispensing holes.

FIG. 1 is an illustration of a perfusion catheter operationally placed in a blood vessel. The catheter of the present invention is shown inserted in blood vessel 2. The catheter is of tubular construction and carries guidewire 3 inside tube 1. At the proximal end an attachment 4 allows to inject medication into tube 1 of the catheter through port 5 and provides an adjustable hemostatic port 5 for guidewire 3. The distal end section e of the catheter has a plurality of holes 7a through 7f arranged in a spiral. The number of holes and the length over which the holes are distributed along distal end section e varies and depends on the application. The sizes of the holes may vary between 0.004" to 0.012". The hole size increases towards tip 9 of distal end section e of the catheter. Radiopaque markers 21 and 23 may be placed next to the first and last holes, holes 7a and 7f, respectively.

In use of the different hole sizes of holes 7a through 7f ensure that the radially dispensed medication per hole and per time is equal over the length of distal end section 8. The spiral arrangement of holes 7a through 7f provides for a distribution of medication in all direction.

The length of the distal end section 8 may be in the range of 0.5 to 30 centimeters. The number of holes 7 may vary between 1 to 30. The sizes of holes 7 may increase from 0.004" to 0.012".

FIG. 2 is; an illustration of the distal end section 8 of the perfusion catheter. Distal end section 8 has 6 holes 7a through 7f of different diameters. Hole sizes increase from right to left, from the catheter side to tip 9 of the catheter. During use of catheter 1 guidewire 3 remains inserted. A valve body 20 is incorporated in the tip end of distal end section 8 (see FIG. 3). The center hole 22 in valve body 20 is large enough not to freely operate guidewire 3, and it is small enough not to let significant amounts of medication leak in axial direction. As will be shown below, guidewire 3 and valve body 20 can be used for a controlled release of medication in axial direction. Radiopaque marker 21 is inserted in distal end section 8 to provide for visualization under fluoroscopy of the location of tip 9. The valve body transitions smoothly from the opaque marker to guide the tip of guidewire 3 while the guidewire advances into marker 21. A second marker 23 may be placed at the other end of distal end section 8. Arrows '4'—'4' indicate the location and direction of the cross-sectional view of FIG. 3.

FIG. 3 is a cross-sectional view of the distal end section of perfusion catheter 1. Holes 7 are arranged in an equally angled displacement along the spiral around distal end section 8 with the smallest diameter hole 7a close to the location '4'—'4' of the cross-sectional view.

FIG. 4 is an illustration of a distal end section of another perfusion catheter. FIG. 5 is a cross-section view of '6'—'6' of the distal end section 51 of FIG. 4. This distal end section 51 has only 4 radially ejecting holes 50a through 50d. Holes 50a through 50d have an angular displacement of 90 degrees.

As shown in FIGS. 2 and 4 tip 9 of the distal end section 8 and tip, 53 of distal end section 51 are chamfered. This feature makes it possible to penetrate a blood clot in a blood vessel without breaking it loose. The preferred chamfer angle is between 15 degree and 45 degree.

In another implementation of tip of a distal end section the guidewire is equipped with a plug 75 which fits to the tip end of valve seat 20 in FIG. 2.

FIG. 6 is a more detailed illustration of the controllable axial ejection valve. Valve seat 71 in distal end section 70 has a center hole 72 of a diameter selected for dispensing a certain amount of medication while the guidewire 73 is in place but not in position to plug center hole 72. Guidewire 73 includes a plug 75 with suitable contour to plug center hole 72 when guidewire 73 is pulled by the operator in the direction of arrow 76. Valve seat 71 may be exchangeable so that a seat can be inserted with a most suitable hole sizes for the particular application. Radiopaque marker 77 may be inserted in the distal end 70 of the catheter, as shown in FIG. 6, or it may be embedded in the tubular structure of distal end 70, or it could be placed outside the tubing of the catheter.

FIG. 7 is an illustration of a catheter and guidewire for controlling radial dispensation of medication. When advancing guidewire 83 enlarged diameter body 85 will be moved towards the end of distal end section 80. When pulling on guidewire 83 in direction of arrow 86 body 85 will be moved inside distal end section 80 and when passing holes 84a to 84e eliminate that hole from distributing medication and any hole distal to body 85. Thus, sliding body 85 inside distal end section 80 allows to control the length over which medication is dispensed inside the vessel. For monitoring the position of body 85 inside the catheter and especially inside distal end section 80 body 85 may include a radiopaque marker.

Figure 8:
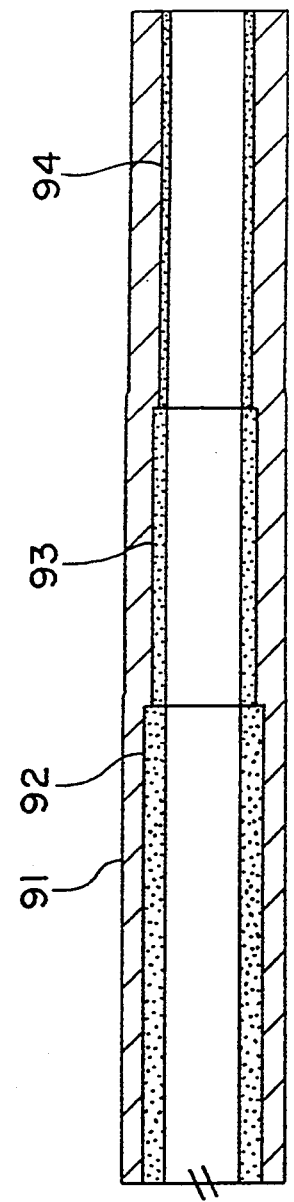
FIG. 8 is an illustration of the structure of the catheter with sections of different flexibility between the proximal and the distal end.

FIG. 8 is an illustration of the structure of the catheter with sections of different flexibility between the proximal and the distal end. The catheter of the present invention has 2 or more segments of different flexibility. Each segment has an inner core tube segment with a certain flexibility characterized by the flexural modulus. Flexural modulus of the material and thickness of the segment determine the flexibility of a segment. All inner segments of a catheter are covered by one outer tube. The thickness of the catheter is determined by the diameter of the inner segment and the outer tube. Both inner segments and outer tube together determine the local flexibility of the catheter. If the inner segment is tapered, the catheter will have a changing diameter and flexibility over the length of the tapered section.

The catheter of the present invention with different flexibility characteristics between proximal and distal ends improves the applicability of the catheter, and allows to have very flexible distal tips compared with the proximal end section. A catheter of the present invention with smooth transitions between sections of different flexibilities reduce the likelihood of kinking during insertion through sharp bends.

FIG. 8 is an illustration of three segments of a catheter with segments of different flexibilities. All three segments share outer tubing 91. The left segment includes inner segment 92, the center segment includes inner segment 93, and the right segment includes inner segment 94. All three inner segments may be of the same material. Because the inner diameter of all inner segments is the same a segment flexibility is dependent on the outer diameter of the particular inner segment. The flexibility can be further changed by selecting different material for the different segments. In FIG. 8 the three inner segments are shown to have different but constant outer diameters, which results in a graduated flexibility over the length of the catheter. A nongraduated change of flexibility can be achieved by tapering the outer diameters of the segments.

The invention disclosed above has been described in detail with respect to one preferred embodiment. It is considered obvious within the scope of the invention and the claims that a skilled artisan may make certain modifications.

What we claim is:

1. A catheter comprising
   an elongated tubular body having a proximal end section, a main section and a distal end section; and
   a port in the proximal end section for supplying medication into said catheter;
   said distal end section having a plurality of radial holes of different diameters for radially ejecting said medication, and a tip located distally in said distal end section and including an axial hole for axially ejecting medication,
   said radial holes being spirally arranged in order of their diameter, with the larger diameter holes being located towards said tip of said distal end section.

2. A catheter device for dispensing medication comprising a catheter device having an elongated tubular body including a main section, a proximal end section and distal end section, a port connected to the proximal end section of said catheter device for receiving said medication to be dispensed through said distal end section;
   said distal end section including a plurality of radial holes of different diameters for radially ejecting said medication, and a tip located distal by in said distal end section and having an axial hole for axially ejecting medication;
   a guidewire having a first end section extending beyond said proximal end of said catheter device, a center section extending along the length and inside of said catheter device, and a second end section extending through said axial hole and beyond said tip of said distal end section; means for supplying medication into said catheter device, and means for moving said guidewire in said catheter device;
   said radial holes being spirally arranged in order of their diameter, with the larger diameter holes being located towards said tip of said distal end section.

3. A catheter device for dispensing medication as claimed in claim 2, wherein said tip is chamfered at an angle suitable for penetrating soft blood clots.

4. A catheter device for dispensing medication as claimed in claim 3, wherein said tip is chamfered at an angle between 15° and 45°.

5. A catheter device for dispensing medication comprising a catheter device having an elongated tubular body including a main section, a proximal end section and a distal end section, a port connected to said proximal end section for receiving said medication;
   said distal end section including a plurality of radial holes of different diameters for radially ejecting said medication, and
   a tip located distally in said distal end section and including a valve seat having an axial hole for axially ejection said medication,
   said radial holes being spirally arranged in order of their diameter, with the larger diameter holes being located towards said tip of said distal end section;
   a guidewire having a first end section extending beyond said proximal end section of said catheter device, a center section extending along the length and inside of said catheter device, and a second end section extending through said axial hole and beyond said tip of said distal end section; and means for moving said guidewire in said catheter device.

6. A catheter device for dispensing medication as claimed in claim 5 wherein said second end section of said guidewire includes an enlarged diameter section with a diameter larger than said axial hole, said enlarged diameter section and said value seat having complementary interfacing surfaces, said enlarged diameter section and said value seat constituting a valve for controlling axial dispensation of said medication.

7. A catheter device for dispensing medication as claimed in claim 5, further including
   a first radiopaque marker for marking the interface of said center section and said distal end section of said catheter device; and a second radiopaque marker in close proximity to said tip for marking the location of the medication dispensing distal end section.

8. A catheter device for dispensing medication as claimed in claim 5, wherein said value seat is exchangeably mounted inside said distal end section and in close proximity to said tip.

9. A catheter device for dispensing medication as claimed in claim 6, wherein said value seat is exchangeable with value seat of a different axial hole size.

10. A catheter device for dispensing medication as claimed in claim 5, wherein said second end of said guidewire has a diameter only slightly smaller than said axial hole, said guidewire, when extending through said axial hole, substantially reduces fluid flow through said axial hole.

11. A catheter device for dispensing medication comprising a catheter device having an elongated tubular body including a main section, a proximal end section and a distal end section;
 a tip having an axial hole for axially dispensing medication, said tip located distally in said distal end section, and
 said distal end section of said catheter device including
  a plurality of radial holes of different diameters for radially dispensing medication, said radial holes being spirally arranged in order of their diameter, with the larger diameter holes being located towards said tip of said distal end section;
a guidewire having first end section extending beyond said proximal end of said catheter device, a center section extending along the length of said catheter device, and a second end section extending through said axial hole and beyond said tip of said distal end section; means for feeding said first end section and said center section of said guidewire into said catheter device; and means for supplying medication into said catheter device; said guidewire including an enlarged diameter body for controlling dispensation of medication through said radial holes including
 said body having a diameter slightly smaller than the inner diameter of said distal end section of said catheter device;
  said body being adapted to move inside said distal end section of said catheter device section from said tip towards said main section upon advancement or retraction at said first end of said guidewire, thereby reducing or increasing the number of radial holes for dispensation of medication.

12. A catheter device for dispensing medication as claimed in claim 11, further including a first radiopaque marker for marking the interface of said center section and said distal end section of said catheter device.

13. A catheter device for dispensing medication as claimed in claim 11, further including
 a first radiopaque marker for marking the interface of said center section and said distal end section of said catheter device; and a second radiopaque marker included in said body for marking the distance over which medication is dispensed.

14. A catheter device for dispensing medication comprising an elongated tubular body having a main section, a distal end section and a plurality of intermediate sections; and means for supplying medication into said catheter device;
 said distal end section having a plurality of radial holes of different diameters for radially ejecting medication, and a tip located dismally in said distal end section and including an axial hole for axially ejecting medication,
 said radial holes being spirally arranged in order of their diameter, with the larger diameter holes being located towards said tip of said distal end section each one of said plurality of intermediate sections having a different characteristic flexibility.

15. A catheter device as claimed in claim 14 wherein each of said sections having in inner tubular segment of a specific flexibility and wherein all of said sections have an outer tube in common.

16. A catheter device as claimed in claim 14 wherein at least one of said intermediate sections having an inner tubular section with linearly changing flexibility along the length of said at least one intermediate section.

17. A catheter device as claimed in claim 14 wherein said elongated tubular body is constructed to be relatively axially rigid in said main section, and progressively more axially flexible along said intermediate sections so as to be most axially flexible in the intermediate section nearest the tip of the distal end section.

* * * * *

UNITED STATES PATENT AND TRADEMARK OFFICE
CERTIFICATE OF CORRECTION

PATENT NO. : 5,380,307
DATED : January 10, 1995
INVENTOR(S) : U. Hiram Chee, et al.

It is certified that error appears in the above-indentified patent and that said Letters Patent is hereby corrected as shown below:

In the abstract, line 2: change "sued" to --used--.

column 2, line 58: insert --in-- prior to "combination".

column 3, line 47: change "5" to --6--.

column 3, line 51: change "end section e" to --end section 8--.

column 3, line 54: change "e of the catheter" to --8 of the catheter-- column 4, line 30: insert --,-- after "4":

column 4, line 31: delete ",".

column 3, line 48, change "e" to --8--.

Claim 2, column 6, line 1: delete "distal by" and insert --distally--.

Claim 8, column 6, line 60: delete "value" and insert --valve--.

Claim 9, column 6, line 64: delete "value" and insert --valve--.

Claim 9, column 6, line 65: delete "value" and insert --valve--.

Signed and Sealed this

Fourth Day of November, 1997

*Attest:*

BRUCE LEHMAN

*Attesting Officer*  *Commissioner of Patents and Trademarks*